United States Patent
Cai et al.

(10) Patent No.: US 9,737,207 B2
(45) Date of Patent: *Aug. 22, 2017

(54) METHOD FOR QUICK SWITCHING TO REALIZE ANTERIOR AND POSTERIOR EYE SEGMENTS IMAGING

(71) Applicant: SHENZHEN CERTAINN TECHNOLOGY CO., LTD., Shenzhen (CN)

(72) Inventors: Shoudong Cai, Shenzhen (CN); Peng Li, Shenzhen (GD); Shuguang Guo, Shenzhen (GD); Xiangsong Dai, Shenzhen (GD); Lei Wu, Shenzhen (GD)

(73) Assignee: SHENZHEN CERTAINN TECHNOLOGY CO., LTD., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/161,722

(22) Filed: May 23, 2016

(65) Prior Publication Data

US 2016/0262609 A1      Sep. 15, 2016

Related U.S. Application Data

(62) Division of application No. 14/124,030, filed on Dec. 5, 2013, now Pat. No. 9,370,300.

(51) Int. Cl.
| | | |
|---|---|---|
| *A61B 3/10* | (2006.01) | |
| *A61B 3/117* | (2006.01) | |
| *A61B 3/14* | (2006.01) | |
| *A61B 3/00* | (2006.01) | |

(Continued)

(52) U.S. Cl.
CPC .......... *A61B 3/1005* (2013.01); *A61B 3/0091* (2013.01); *A61B 3/102* (2013.01); *A61B 3/1173* (2013.01); *A61B 3/12* (2013.01); *A61B 3/14* (2013.01); *G01B 9/02028* (2013.01);
(Continued)

(58) Field of Classification Search
CPC ..... A61B 3/1005; A61B 3/0091; A61B 3/102; A61B 3/1173; A61B 3/12; A61B 3/14; G01B 9/02028; G01B 9/02064; G01B 9/02091; G01B 2290/35
USPC ........ 351/205, 206, 210, 246, 221; 356/450, 356/477, 482, 496, 498, 500, 503, 511, 356/512, 513, 514, 515
See application file for complete search history.

(56) References Cited

U.S. PATENT DOCUMENTS

2012/0200859 A1* 8/2012 Breitenstein ........... A61B 3/102
356/479

* cited by examiner

*Primary Examiner* — Bumsuk Won
*Assistant Examiner* — Wen Huang

(57) ABSTRACT

It is provided a method for quick switching to realize anterior and posterior eye segments imaging, which can realize quick switch and real-time image for locations at different depths. On one hand, with an ability of quick switch, objects at different depths can be measured, and the detection scope of the OCT system can be enhanced; the switch system is able to work stably and change positions accurately without influencing the signal-to-noise ratio of the system. On the other hand, the light beam can be respectively focalized at different locations. Thus, high quality of anterior and posterior eye segments imaging can be achieved with a relatively high lateral resolution for human eyes having different ametropia. Furthermore, based (Continued)

on the anterior and posterior eye segments imaging, an ability of real-time eye axial length measurement can be added.

4 Claims, 4 Drawing Sheets

(51) Int. Cl.
  *A61B 3/12* (2006.01)
  *G01B 9/02* (2006.01)
(52) U.S. Cl.
  CPC ..... G01B 9/02064 (2013.01); G01B 9/02091 (2013.01); *G01B 2290/35* (2013.01)

METHOD FOR QUICK SWITCHING TO REALIZE ANTERIOR AND POSTERIOR EYE SEGMENTS IMAGING

CROSS REFERENCE TO RELATED APPLICATIONS

This application is a divisional application of a commonly-assigned application entitled "OPHTHALMIC OPTICAL COHERENCE TOMOGRAPHY SYSTEM AND METHOD FOR QUICK SWITCHING TO REALIZE ANTERIOR AND POSTERIOR EYE SEGMENTS IMAGING", filed on Dec. 5, 2013 with application Ser. No. 14/124,030. The disclosure of the above-identified application is incorporated herein by reference.

FIELD OF THE INVENTION

The invention relates to opto-electronics technical field, and in particular, to an ophthalmic optical coherence tomography system and a method for quick switching to realize anterior and posterior eye segments imaging.

BACKGROUND OF THE INVENTION

Eye axial length is a primary issue for judging eye ametropia. It is also an important indication for discriminating true myopia and pseudomyopia, and for computing parameters of an artificial crystal for a cataract operation.

In existing art, methods for measuring an eye axial length include A-scan ultrasonic measurement and optical measurement. Existing A-scan ultrasonic measurement takes advantage of ultrasonic ranging principle. However, it is necessary to directly touch human eye with a probe in the A-scan ultrasonic measurement. Moreover, resolution of A-scan ultrasonic measurement is relatively low and thus is incapable of measurement with a sufficient accuracy. In optical measurement, an eye axis length is measured based on the theory of dual-wavelength light wave interference. Optical Coherence Tomography (OCT) is a newly developing optical imaging technique. Patent CN200710020707.9 discloses a method of measuring an eye axial length with OCT, and eye axial length measurement for human eye and eyes of various kinds of living animals can be implemented with this method. However, the inventor, during the practice of the invention, discovered that the existing art at least has the following disadvantages. Firstly, the optical path is adjusted by using a movable probe moved by a stepping motor to realize imaging of the cornea and fundus. It takes a certain time for the motor to move back and forth. Thus, it is incapable of quickly switching between the anterior and posterior eye segments and realizing real-time imaging. Furthermore, since the measured object will shake its eyes, the measurement of eye axial length is inaccurate with a large error. Secondly, the imaging quality is bad due to the fact that the cornea and fundus have different shapes and it is unable for a single probe to focus at both of the two locations.

SUMMARY OF THE INVENTION

A technical problem that solved by embodiments of the present invention is how to provide an ophthalmic optical coherence tomography system and a method of measuring the length of an eye axis, in which imaging at one time and quick switching for locations at different depths can be realized, and on this basis, the eye axial length can be measured accurately.

To solve the above mentioned technical problem, it is provided an ophthalmic optical coherence tomography system according to an embodiment of the present invention. The ophthalmic optical coherence tomography system comprises: an ophthalmic optical coherence tomography system, comprising: an OCT interferometer primary module and a sample arm module, wherein, the OCT interferometer primary module comprises an OCT light source, a fiber coupler, a reference arm, a detection module, an X-direction scanning unit, and a Y-direction scanning unit; the sample arm module comprises an anterior eye segment imaging module and a posterior eye segment imaging module; and wherein:

light output by the OCT light source is provided to the sample arm module and the reference arm via the fiber coupler; the reference arm reflects the light received by the reference arm to the fiber coupler; the Y-direction scanning unit is rotatable; when the Y-direction scanning unit is at a first rotation angle, the Y-direction scanning unit reflects light received by the X-direction scanning unit into the anterior eye segment imaging module; when the Y-direction scanning unit is at a second rotation angle, the Y-direction scanning unit reflects the light received by the X-direction scanning unit into the posterior eye segment imaging module; the fiber coupler receives light scattered back by the sample arm, and the received light interferes with the light reflected back by the reference arm; and the detection module is used for detecting the interfered light.

Wherein, the anterior eye segment imaging module comprises: a total-reflection mirror, a rotatable-adjustable total-reflection mirror, a dichroic mirror, and a fundus lens, and wherein:

when the Y-direction scanning unit is rotated at the first rotation angle, the Y-direction scanning unit reflects light transmitted from the X-direction scanning unit to the total-reflection mirror; the total-reflection mirror reflects the light to the rotatable-adjustable total-reflection mirror; the rotatable-adjustable total-reflection mirror is rotatably adjusted correspondingly to a rotation of the Y-direction scanning unit and cooperates with the Y-direction scanning unit to reflect the light transmitted on the rotatable-adjustable total-reflection mirror to the dichroic mirror; the dichroic mirror reflects the light to the fundus lens; and the light is transmitted through the fundus lens into a human eye to be examined.

Wherein, the anterior eye segment imaging module further comprises at least one relay lens, and wherein:

the at least one relay lens is between the Y-direction scanning unit and the total-reflection mirror; in this case, when the Y-direction scanning unit is rotated at a first rotation angle, the Y-direction scanning unit reflects the light from the X-direction scanning unit to the total-reflection mirror via the relay lens; or the at least one relay lens is between the total-reflection mirror and the rotatable-adjustable total-reflection mirror; in this case, the total-reflection mirror reflects the light from the X-direction scanning unit to the rotatable-adjustable total-reflection mirror via the relay lens.

Wherein, the posterior eye segment imaging module comprises: an optical path adjustment unit, a refraction adjustment unit, a rotatable-adjustable total-reflection mirror, a dichroic mirror, and a fundus lens, and wherein:

when the Y-direction scanning unit is rotated at a second rotation angle, the Y-direction scanning unit reflects light transmitted from the X-direction scanning unit to the optical path adjustment unit; the optical path adjustment unit reflects the light to the rotatable-adjustable total-reflection mirror via the refraction adjustment unit; the rotatable-adjustable total-reflection mirror is rotatably adjusted correspondingly to the rotation of the Y-direction scanning unit and cooperates with the Y-direction scanning unit to reflect the light transmitted on the rotatable-adjustable total-reflection mirror to the dichroic mirror; the dichroic mirror reflects the light to the fundus lens; and the light is transmitted through the fundus lens into the human eye to be examined.

Wherein, the system further comprises:

an iris imaging module, which comprises: a fundus lens, a dichroic mirror, an iris dichroic mirror, an objective lens, and a camera, wherein, when the light output by the light source illuminates a cornea of a human eye to be examined and is reflected on the cornea, the reflected light is transmitted though the fundus lens and the dichroic mirror and reaches the iris dichroic mirror; the iris dichroic mirror reflects the light to the objective lens; and the reflected light is transmitted to the camera via the objective lens and is imaged by the camera.

The system further comprising a fixation optical module, wherein:

the fixation optical module comprises: a fixation device, a lens, a total-reflection mirror, a refraction compensating lens, a dichroic mirror, and a fundus lens; after focalized by the lens, light from the fixation device is reflected to the refraction compensating lens by the total-reflection mirror, transmitted to the iris dichroic mirror in the iris imaging module via the refraction compensating lens, transmitted to the dichroic mirror and the fundus lens through the iris dichroic mirror, and transmitted through the fundus lens into a human eye to be examined.

Wherein, the optical path adjustment unit comprises four total-reflection mirrors, and wherein two of the total-reflection mirrors are fixed, and the other two of the total-reflection mirrors are removable total-reflection mirrors; during adjustment of optical path, the optical path is adjusted by keeping the two of the total-reflection mirrors fixed and moving the other two removable total-reflection mirrors.

Wherein, the optical path adjustment unit further comprises two total-reflection mirrors and a removable retroreflector; during adjustment of optical path, the optical path is adjusted by keeping the two total-reflection mirrors fixed and moving the removable retroreflector.

Wherein, the total-reflection mirror in the Y-direction scanning unit is a galvanometer.

Wherein, the fixation device in the fixation optical module comprises an LCD or an OLED.

Wherein, an adjustment amount of the optical path adjustment unit is obtained by a location sensor, the location sensor being fixed on the removable total-reflection mirror or the removable retroreflector in the optical path adjustment unit.

Correspondingly, according to an embodiment of the invention, it is also provided a method for quick switching to realize anterior and posterior eye segments imaging, comprising:

reflecting light transmitted from the X-direction scanning unit to the total-reflection mirror with the Y-direction scanning unit when the Y-direction scanning unit is rotated at the first rotation angle; reflecting the light to the rotatable-adjustable total-reflection mirror with the total-reflection mirror, the rotatable-adjustable total-reflection mirror being rotatably adjusted correspondingly to a rotation of the Y-direction scanning unit and cooperating with the Y-direction scanning unit to reflect the light transmitted on the rotatable-adjustable total-reflection mirror to the dichroic mirror; reflecting the light to the fundus lens with the dichroic mirror; transmitting the light through the fundus lens into a human eye to be examined;

reflecting the light transmitted from the X-direction scanning unit to the optical path adjustment unit with the Y-direction scanning unit when the Y-direction scanning unit is rotated at a second rotation angle; reflecting the light to the rotatable-adjustable total-reflection mirror via the refraction adjustment unit with the optical path adjustment unit, the rotatable-adjustable total-reflection mirror being rotatably adjusted correspondingly to the rotation of the Y-direction scanning unit and cooperating with the Y-direction scanning unit to reflect the light transmitted on the rotatable-adjustable total-reflection mirror to the dichroic mirror; reflecting the light to the fundus lens with the dichroic mirror; and transmitting the light through the fundus lens into the human eye to be examined.

Wherein, the method comprises:

when the system is performing anterior eye segment imaging, obtaining an optical path length that light travels after leaving the fiber and before reaching a cornea of the human eye to be examined in the anterior eye segment imaging, the optical path length being a fixed length of anterior eye segment optical path plus a distance A between a peak of the cornea and a peak of image in an OCT image of anterior eye segment, wherein the fixed length of anterior eye segment optical path is an intrinsic parameter of the system, and the distance A between the peak of the cornea and the peak of image in the OCT image of anterior eye segment is obtained by analyzing the OCT image;

when the system is performing posterior eye segment imaging, obtaining an optical path length that light travels after leaving the fiber and before reaching a retina of the human eye to be examined in the posterior eye segment imaging, the optical path length being a fixed length of posterior eye segment optical path plus an optical path adjustment amount plus a distance B between a peak of image and a macula fovea in an OCT image of posterior eye segment, wherein the fixed length of posterior eye segment optical path is an intrinsic parameter of the system, and the distance B between the peak of image and the macula fovea in the OCT image of posterior eye segment is obtained by analyzing the OCT image;

calculating the difference between the optical path length obtained in anterior eye segment imaging and the optical path length obtained in posterior eye segment imaging, and obtaining an optical length of examined eye axis, wherein the optical length of eye axis is: (the fixed length of posterior eye segment optical path plus an optical path adjustment amount plus the distance B between the peak of image and the macula fovea in the OCT image of posterior eye segment) minus (the fixed length of anterior eye segment optical path plus the distance A between the peak of the cornea and the peak of image in the OCT image of anterior eye segment).

Wherein, the method comprises:

when the system is performing anterior eye segment imaging, collecting an anterior surface of corneal in a cornea image in the anterior eye segment imaging optical path, and changing the length of posterior eye segment imaging optical path by adjusting a removable total-reflection mirror or a removable retroreflector in the optical path adjustment unit, so that a surface of crystalline lens is measured to obtain an optical depth of anterior chamber, the optical depth of anterior chamber being a distance between the cornea and an anterior surface of crystalline lens, wherein the anterior surface of corneal is obtained with a anterior eye segment imaging system and the anterior surface of crystalline lens is obtained with a posterior eye segment imaging system.

Wherein, the method comprises:

when the system is performing anterior eye segment imaging, collecting a cornea image in the anterior eye segment imaging module; changing an optical path of posterior eye segment imaging module by adjusting a removable total-reflection mirror or a removable retroreflector in the optical path adjustment unit, so that a posterior surface of crystalline lens is measured with the posterior eye segment imaging module; obtaining a distance between the cornea and the posterior surface of crystalline lens; and obtaining an optical thickness of the crystalline lens by subtracting the distance by the optical depth of anterior chamber; or scanning an anterior surface of crystalline lens with the anterior eye segment imaging module and concurrently collecting the posterior surface of crystalline lens with the posterior eye segment imaging module, to obtain the optical thickness of the crystalline lens, the optical thickness of the crystalline lens being equal to subtracting the posterior surface of crystalline lens collected with the posterior eye segment imaging module by the anterior surface of crystalline lens scanned with the anterior eye segment imaging module.

In implementation of the invention, quick switch and real-time image for locations at different depths can be realized. On one hand, with an ability of quick switch, objects at different depths can be measured, and the detection scope of the OCT system can be enhanced. The switch system is able to work stably and change positions accurately without influencing the signal-to-noise ratio of the system. On the other hand, the light beam can be respectively focalized at different locations. Thus, high quality of anterior and posterior eye segments imaging can be achieved with a relatively high lateral resolution for human eyes having different ametropia. Furthermore, based on the anterior and posterior eye segments imaging, an ability of real-time eye axial length measurement can be added.

BRIEF DESCRIPTION OF THE DRAWINGS

In order to illustrate the embodiments or existing technical solutions more clearly, a brief description of drawings that assists the description of embodiments of the invention or existing art will be provided below. It would be apparent that the drawings in the following description are only for some embodiments of the invention. A person having ordinary skills in the art will be able to obtain other drawings on the basis of these drawings without paying any creative work.

DETAILED DESCRIPTION OF ILLUSTRATED EMBODIMENTS

Technical solutions in embodiments of the present invention will be illustrated clearly and entirely with the aid of the drawings in the embodiments of the invention. It is apparent that the illustrated embodiments are only some embodiments of the invention instead of all of them. Other embodiments that a person having ordinary skills in the art obtains based on the illustrated embodiments of the invention without paying any creative work should all be within the protection scope sought by the present invention.

Figure 1:
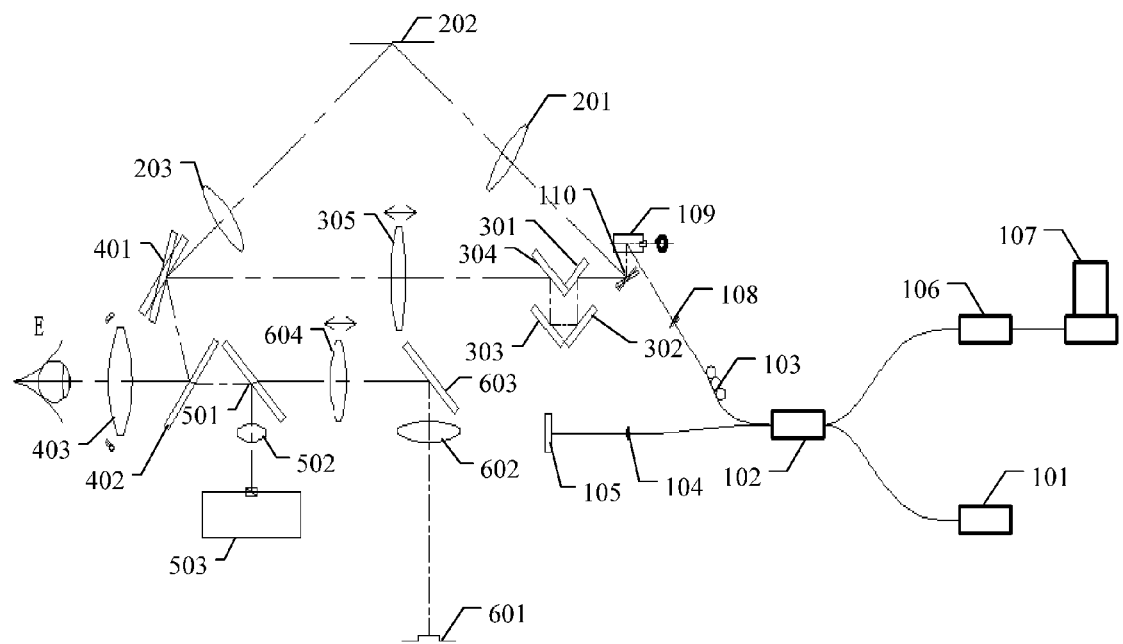
FIG. 1 is a first schematic structural diagram of an ophthalmic optical coherence tomography system according to an embodiment of the invention.

FIG. 1 is a first schematic structural diagram of an ophthalmic optical coherence tomography system according to an embodiment of the invention. As shown in FIG. 1, the ophthalmic optical coherence tomography system comprises: an ophthalmic optical coherence tomography (OCT) interferometer primary module and a sample arm module. The OCT interferometer primary module includes an OCT light source 101, a fiber coupler 102, a reference arm 104, a detection module 106, an X-direction scanning unit 109, and a Y-direction scanning unit 110. The sample arm module comprises an anterior eye segment imaging module and a posterior eye segment imaging module.

Light output by the OCT light source 101 is provided to the sample arm module and the reference arm 104 via the fiber coupler 102. The reference arm 104 reflects the received light by it to the fiber coupler 102. The X-direction scanning unit 109 receives the light output by the OCT light source 101, and the Y-direction scanning unit 110 is rotatable. When the Y-direction scanning unit 110 is at a first rotation angle, it reflects the light received by the X-direction scanning unit 109 into the anterior eye segment imaging module. When the Y-direction scanning unit 110 is at a second rotation angle, it reflects the light received by the X-direction scanning unit 109 into the posterior eye segment imaging module. The fiber coupler 102 receives light scattered back by the sample arm, and the received light interferes with the light reflected by the reference arm 104. The detection module 106 is used for detecting the interfered light, which will be processed and displayed by the computer 107.

Specifically, in one embodiment of the invention, when the OCT light source 101 is a low coherence light source, the detector in the detection module 106 is a spectrometer (the system is a frequency domain OCT); and when the OCT light source 101 is a frequency sweep light source, the detector is a high-speed photoelectric detector (the system is a frequency sweep OCT). The reference arm 104 includes a reference mirror 105 and a collimating lens 108, wherein, in the reference arm 104, the reference mirror 105 reflects the received light output by the OCT light source back to the fiber coupler 102. The collimating lens 108 routes the light output by the OCT light source 10 to the X-direction scanning unit 109. The Y-direction scanning unit 110 is rotatable. With the rotation of the Y-direction scanning unit 110, the light from the X-direction scanning unit 109 is reflected to an imaging module corresponding to the rotation angle. That is, when the Y-direction scanning unit 110 is at a first rotation angle, the light received by the X-direction scanning unit 109 is reflected into the anterior eye segment imaging module; and when the Y-direction scanning unit 110 is at a second rotation angle, the light received by the X-direction scanning unit 109 is reflected into the posterior eye segment imaging module. The OCT interferometer primary module further comprises a polarization controller 103, which is connected with the fiber coupler 102 and used for receiving the light reflected back by the sample arm module and transmitting it to the fiber coupler 102.

It should be made clear that the sample arm module includes the anterior eye segment imaging module and the posterior eye segment imaging module, wherein the anterior eye segment imaging module comprises: a total-reflection mirror 202, a rotatable-adjustable total-reflection mirror 401, a dichroic mirror 402, and a fundus lens 403. When rotated at the first rotation angle, the Y-direction scanning unit 110 reflects the light from the X-direction scanning unit 109 back to the total-reflection mirror 202. Then, the light is reflected to the rotatable-adjustable total-reflection mirror 401 by the total-reflection mirror 202. The rotatable-adjustable total-reflection mirror 401 is rotatably adjusted correspondingly to the rotation of the Y-direction scanning unit 110 and cooperates with the Y-direction scanning unit 110 to reflect the light sent on the rotatable-adjustable total-reflection mirror 401 to the dichroic mirror 402. The light is then reflected to the fundus lens 403 by the dichroic mirror 402 and transmitted through the fundus lens 403 into a human eye E which is to be examined.

It should be made clear that the sample arm module includes the anterior eye segment imaging module and the posterior eye segment imaging module. The posterior eye segment imaging module comprises the rotatable-adjustable total-reflection mirror 401, the dichroic mirror 402, and the fundus lens 403 which has been included in the anterior eye segment imaging module. Further, the posterior eye segment imaging module additionally comprises an optical path adjustment unit and a refraction adjustment unit 305. When rotated at the second rotation angle, the Y-direction scanning unit 110 reflects the light from the X-direction scanning unit 109 to a first total-reflection mirror 301 in the optical path adjustment unit. Then, reflected by the second total-reflection mirror 302, the third total-reflection mirror 303, and the fourth total-reflection mirror 304, the light is reflected by the optical path adjustment unit and transmitted to the rotatable-adjustable total-reflection mirror 401 via the refraction adjustment unit 305. The rotatable-adjustable total-reflection mirror 401 is rotated correspondingly to the rotated angle of the Y-direction scanning unit 110 and cooperates with the Y-direction scanning unit 110 to reflect the light transmitted on the rotatable-adjustable total-reflection mirror 401 to the dichroic mirror 402. The light is then reflected to the fundus lens 403 by the dichroic mirror 402 and transmitted through the fundus lens 403 into the human eye E to be examined.

It should be made clear that the anterior eye segment imaging module and the posterior eye segment imaging module share the same rotatable-adjustable total-reflection mirror 401, dichroic mirror 402, and fundus lens 403.

It should be made clear that the ophthalmic optical coherence tomography system further includes an iris imaging module which comprises: an iris dichroic mirror 501, an objective lens 502, and a camera 503. When the light from the light source illuminates the cornea of a human eye to be examined and is reflected on the cornea, the reflected light travels though the fundus lens 403 and the dichroic mirror 402 and reaches the iris dichroic mirror 501. The iris dichroic mirror 501 reflects the light to the objective lens 502. The reflected light is than transmitted to the camera 503 via the objective lens 502 and is imaged by the camera 503.

It should be made clear that the ophthalmic optical coherence tomography system further includes a fixation optical module which comprises: a fixation device 601, a lens 602, a total-reflection mirror 603, and a refraction compensating lens 604. After focalized by the lens 602, light from the fixation device 601 is reflected to the refraction compensating lens 604 by the total-reflection mirror 603. Then, the light is transmitted to the iris dichroic mirror 501 via the refraction compensating lens 604, routed to the dichroic mirror 402 and the fundus lens 403 through the iris dichroic mirror 501, and transmitted through the fundus lens 403 into the human eye to be examined.

The ophthalmic optical coherence tomography system provided in one embodiment of the invention can achieve not only posterior eye segment imaging but also anterior eye segment imaging. With the Y-direction scanning unit 110 cooperating with the rotatable-adjustable total-reflection mirror 401, namely, the rotatable-adjustable total-reflection mirror 401 is rotated simultaneously and correspondingly with the rotation of the Y-direction scanning unit 110, a quick, accurate, and real-time imaging of locations at different depths can be achieved as well as switching between anterior and posterior segments imaging systems. Furthermore, a function of measuring the eye axial length can be added on the basis of achieving imaging of anterior eye segment and posterior eye segment.

Figure 2:
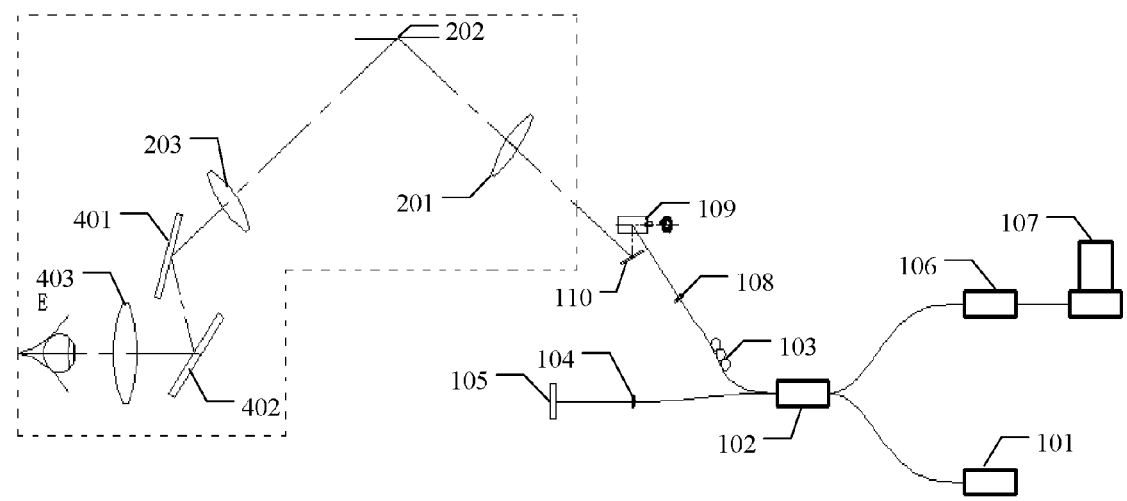
FIG. 2 is a schematic structural diagram of a module for realizing anterior eye segment imaging in an ophthalmic optical coherence tomography system according to an embodiment of the invention.

FIG. 2 is a schematic structural diagram of a module for realizing anterior eye segment imaging in an ophthalmic optical coherence tomography system according to an embodiment of the invention. As shown in FIG. 2, the anterior eye segment imaging module comprises: a total-reflection mirror 202, a rotatable-adjustable total-reflection mirror 401, a dichroic mirror 402, and a fundus lens 403. When rotated at the first rotation angle, the Y-direction scanning unit 110 reflects the light from the X-direction scanning unit 109 back to the total-reflection mirror 202. Then, the light is reflected to the rotatable-adjustable total-reflection mirror 401 by the total-reflection mirror 202. The rotatable-adjustable total-reflection mirror 401 is rotatably adjusted correspondingly to the rotation of the Y-direction scanning unit 110 and cooperates with the Y-direction scanning unit 110 to reflect the light sent on the rotatable-adjustable total-reflection mirror 401 to the dichroic mirror 402. The light is then reflected to the fundus lens 403 by the dichroic mirror 402 and transmitted through the fundus lens 403 into a human eye E which is to be examined.

It should be made clear that the anterior eye segment imaging module further comprises at least one relay lens.

Wherein, there is at least one relay lens between the Y-direction scanning unit 110 and the total-reflection mirror 202. In this case, when Y-direction scanning unit 110 is rotated at the first rotation angle, the Y-direction scanning unit reflects the light from the X-direction scanning unit 109 to the total-reflection mirror 202 via the relay lens.

Optionally, there is at least one relay lens between the total-reflection mirror 202 and the rotatable-adjustable total-reflection mirror 401. In this case, the total-reflection mirror 202 reflects the light from the X-direction scanning unit 109 to the rotatable-adjustable total-reflection mirror 401 via the relay lens.

In one embodiment of the invention, preferably, the anterior eye segment imaging optical path comprises two relay lenses, i.e. a first relay lens 201 and a second relay lens 203. The first relay lens 201 is between the total-reflection mirror 202 and the Y-direction scanning unit 110, and the second relay lens 203 is between the total-reflection mirror 202 and the rotatable-adjustable total-reflection mirror 401. In this case, when rotated at the first rotation angle, the Y-direction scanning unit 110 reflects the light from the X-direction scanning unit 109 to the total-reflection mirror 202 via the first relay lens 201. Then, the light is reflected by the total-reflection mirror 202, transmitted through the second relay lens 203, and transmitted to the rotatable-adjustable total-reflection mirror 401. The light is then reflected to the fundus lens 403 by the dichroic mirror 402. In the end, the light travels through the human eye E and is focalized at the fundus.

Specifically, in one embodiment of the invention, the rotatable-adjustable total-reflection mirror 401 and the Y-direction scanning unit 110 are concurrently controlled by a computer. The Y-direction scanning unit is controlled by the computer to rotate at the first rotation angle. Here, the orientation of the Y-direction scanning unit is able to exactly make the angle between an incident light and a reflected light to be β. Concurrently, the computer controls the rotatable-adjustable total-reflection mirror 401 to rotate correspondingly to the first rotation angle of the Y-direction scanning unit 110 and to cooperate with the Y-direction scanning unit to realize anterior eye segment imaging. After routed through the Y-direction scanning unit 110, the light is transmitted to the total-reflection mirror 202 via the first relay lens 201. Then, the light is reflected by the total-reflection mirror 202, transmitted through the second relay lens 203, and transmitted to the rotatable-adjustable total-reflection mirror 401. The light is then reflected to the fundus lens 403 by the dichroic mirror 402. In the end, the light travels through the human eye E and is focalized at the fundus.

It should be make clear that, in one embodiment of the invention, the Y-direction scanning unit 110 serves not only to scan in one dimensional but also to switch the optical path. In one embodiment of the invention, the Y-direction scanning unit 110 is a galvanometer or utilizes other high-accuracy orientation mechanism, so that the need of quick switch between optical paths in the system can be satisfied. When measuring the fundus, by rotating the Y-direction scanning unit 110, the optical path is reflected to the total-reflection mirror 301 from the X-direction scanning unit 109 and the light turns for an angle of α. When measuring the cornea, by rotating the Y-direction scanning unit 110, the optical path is reflected to the first relay lens 201 from the X-direction scanning unit 109 and the light turns for an angle of β. The rotatable-adjustable total-reflection mirror 401 is rotated correspondingly to the rotation of the Y-direction scanning unit 110. The Y-direction scanning unit 110 and the rotatable-adjustable total-reflection mirror 401 cooperates with each other so that the quick switch between the anterior and posterior eye segment imaging optical paths can be realized.

Figure 3:
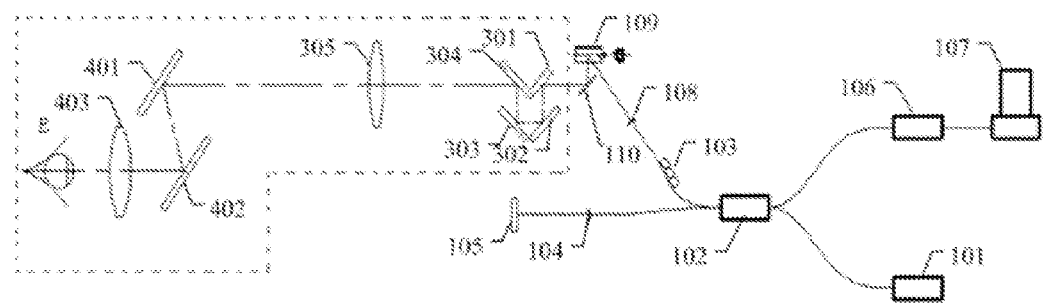
FIG. 3 is a schematic structural diagram of a module for realizing posterior eye segment imaging in an ophthalmic optical coherence tomography system according to an embodiment of the invention.

FIG. 3 is a schematic structural diagram of a module for realizing posterior eye segment imaging in an ophthalmic optical coherence tomography system according to an embodiment of the invention. As shown in FIG. 3, the posterior eye segment imaging module comprises the rotatable-adjustable total-reflection mirror 401, the dichroic mirror 402, and the fundus lens 403 which has been included in the anterior eye segment imaging module. Further, the posterior eye segment imaging module additionally comprises an optical path adjustment unit and a refraction adjustment unit 305. When rotated at the second rotation angle, the Y-direction scanning unit 110 reflects the light from the X-direction scanning unit 109 to a first total-reflection mirror 301 in the optical path adjustment unit. Then, reflected by the second total-reflection mirror 302, the third total-reflection mirror 303, and the fourth total-reflection mirror 304, the light is reflected by the optical path adjustment unit and transmitted to the rotatable-adjustable total-reflection mirror 401 via the refraction adjustment unit 305. The rotatable-adjustable total-reflection mirror 401 and the Y-direction scanning unit 110 cooperates with each other to accomplish the posterior eye segment imaging module.

Specifically, the rotatable-adjustable total-reflection mirror 401 and the Y-direction scanning unit 110 are concurrently controlled by a computer. When the Y-direction scanning unit 110 is rotated at the second rotation angle, the rotatable-adjustable total-reflection mirror 401 is correspondingly rotated at the same time. That is, the rotatable-adjustable total-reflection mirrors 401 and the Y-direction scanning unit 110 cooperates with each other to accomplish the posterior eye segment imaging module. In one embodiment of the invention, the Y-direction scanning unit is controlled by the computer to rotate at the second rotation angle. Here, the orientation of the Y-direction scanning unit is able to exactly make the angle between an incident light and a reflected light to be α. Light transmitted from the X-direction scanning unit 109 is reflected to the first total-reflection mirror 301 by the Y-direction scanning unit 110. Then, the light is reflected by the second total-reflection mirror 302, the third total-reflection mirror 303, and the fourth total-reflection mirror 304. Such that, the light is reflected to the rotatable-adjustable total-reflection mirror 401 via the refraction adjustment unit 305 by the fourth total-reflection mirror 304. The light is then reflected to the fundus lens 403 via the dichroic mirror 402. That is, during the OCT imaging of fundus, it is required that the OCT light beam is localized at the fundus when the scanning galvanometer is motionless and the central light beam of the scanning light beam is focalized at the pupil when the galvanometer is scanning.

It should be made clear that, when measuring the fundus, since different human eyes have different eye axial lengths but the reference arm 104 in the OCT imaging module is unadjustable, it is necessary to incorporate an optical path adjustment unit into the optical path for fundus in the posterior eye segment imaging module. If the optical path adjustment mechanism is implemented by, for example, a stepping motor moving back and forth or other ways, before the two-dimensional galvanometer in the optical path adjustment unit, it is the mechanical system movement to change the optical path. This will introduce Doppler Effect and thus reduce the signal-to-noise ratio of the system. In order to solve this problem, the optical path adjustment unit is added into the optical path of fundus after the two-dimensional galvanometer in the optical path adjustment unit in the invention. The optical path adjustment unit comprises four total-reflection mirrors, and wherein two of the total-reflection mirrors are fixed, and the other two of the total-reflection mirrors are removable total-reflection mirrors. That is, the first total-reflection mirror 301 and the fourth total-reflection mirror 304 are fixed, while the second total-reflection mirror 302 and the third total-reflection mirror 303 are movable total-reflection mirrors. During adjustment of optical path, the optical path is adjusted by keeping the two of the total-reflection mirrors fixed, namely, keeping the first total-reflection mirror 301 and the fourth total-reflection mirror 304 fixed, and moving the other two removable total-reflection mirrors, namely, moving the second total-reflection mirror 302 and the third total-reflection mirror 303, so that, for different human eyes, by adjusting the removable total-reflection mirrors, i.e. the second total-reflection mirror 302 and the third total-reflection mirror 303 and determining the length difference between the optical paths for anterior and posterior eye segments, Doppler Effect would not be introduced when performing the quick switching.

Figure 4:
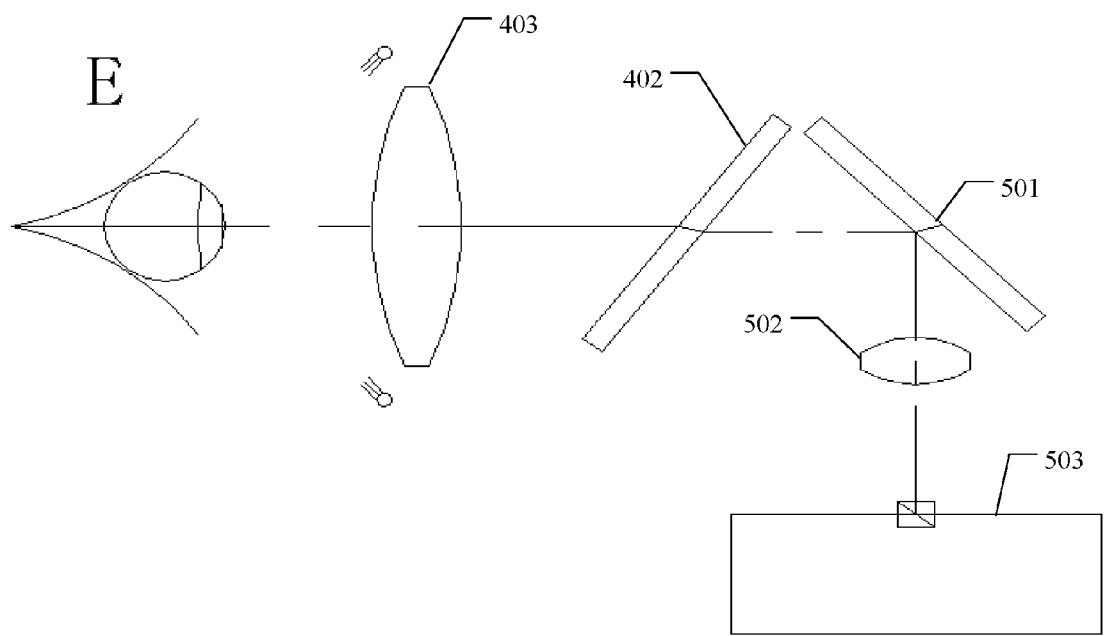
FIG. 4 is a schematic structural diagram of an iris imaging module in an ophthalmic optical coherence tomography system according to an embodiment of the invention.

On the other hand, in one embodiment of the invention, the optical path adjustment unit further comprises two total-reflection mirrors and a removable retroreflector; during adjustment of optical path, the optical path is adjusted by keeping the two total-reflection mirrors fixed and moving the removable retroreflector FIG. 4 is a schematic structural diagram of an iris imaging module in an ophthalmic optical coherence tomography system according to an embodiment of the invention. As shown in FIG. 4, the iris imaging module comprises a fundus lens 403, a dichroic mirror 402, an iris dichroic mirror 501, an objective lens 502, and a camera 503, wherein, when the light output by the light source illuminates a cornea of a human eye E to be examined and is reflected on the cornea, the reflected light is transmitted though the fundus lens 403 and the dichroic mirror 402 and reaches the iris dichroic mirror 501; the iris dichroic mirror 501 reflects the light to the objective lens 502; and the reflected light is transmitted to the camera 503 via the objective lens 502 and is imaged by the camera 503.

Specifically, a monitor optical path in the iris imaging module guides the doctor to operate the instrument and know information related to the person being examined. A chin support system is used to keep the eye being examined fixed and make the fixation mark from the fixation optical module to be fixed seen in the eye E being examined. The examinee is observing the display of the computer 107 in the OCT interferometer primary module while controlling the movement of the chin support system with a joystick, so that the cornea of the eye E being examined can be taken by the camera 503 in the iris imaging module and an image of the cornea is shown in the display of the computer 107 in the OCT interferometer primary module to direct the doctor to operate the instrument and know information related to the human eye being examined.

It should be made clear that the iris dichroic mirror 501 can not only reflect the illuminating light from the illuminating light source in the iris imaging module but also transmit the fixation light output by the fixation device 601 in the fixation optical module.

It should be made clear that the light output by the illuminating light source can be near-infrared light with a wavelength of 780 nm.

Figure 5:
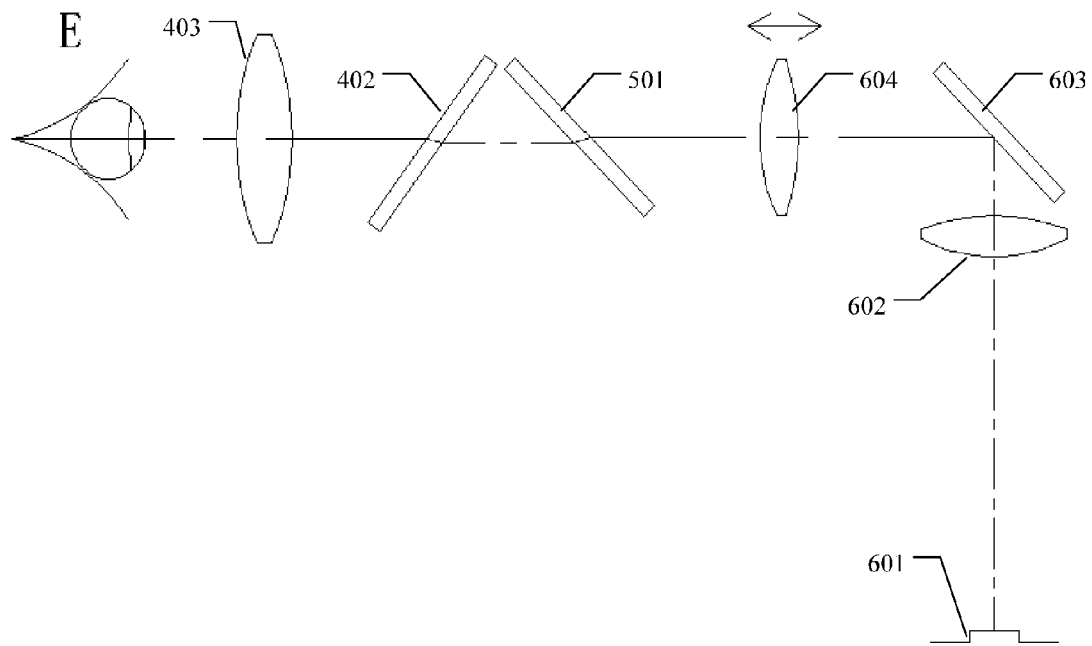
FIG. 5 is a schematic structural diagram of a fixation optical module in an ophthalmic optical coherence tomography system according to an embodiment of the invention.

FIG. 5 is a schematic structural diagram of a fixation optical module in an ophthalmic optical coherence tomography system according to an embodiment of the invention. As shown in FIG. 5, the fixation optical module comprises: a fixation device 601, a lens 602, a total-reflection mirror 603, a refraction compensating lens 604, a dichroic mirror 402, and a fundus lens 403. The light from the fixation device 601 is focalized by the lens 602, reflected to the refraction compensating lens 604 by the total-reflection mirror 603, transmitted to the iris dichroic mirror 501 in the iris imaging module via the refraction compensating lens 604, routed to the dichroic mirror 402 and the fundus lens 403 through the iris dichroic mirror 501, and transmitted into the human eye E to be examined via the fundus lens 403.

Specifically, in an embodiment of the invention, an internal fixation mark can be used to change the fixation position of the human eye E to be examined. The internal fixation mark can be moved up and down, left and right, to meet the examining requirement of the human eye at different positions. When implementing posterior eye segment imaging, the refraction adjustment unit 305 in the posterior eye segment imaging module and the refraction compensating lens 604 in the fixation optical module can be concurrently controlled by a computer.

If the fixation point is fixed and does not move, the clarity of the fixation point is different for different human eyes, causing the examined human uncomfortable during the eye fixation. Thus, after the refraction of OCT light path in the posterior eye segment imaging module is adjusted by the refraction adjustment unit 305, the light path can be focalized on the fundus retina, which enables the human eye to see the scanning line clearly.

In an embodiment of the invention, in order for different human eyes to see clearly the scanning line, a refraction adjustment mechanism is introduced for the fixation point by the refraction compensating lens 604 in the fixation optical module, for the sole sake that different human eyes can see clearly. However, if the fixation optical path is added after the refraction adjustment unit 305 in the posterior eye segment imaging module, the OCT optical path in the posterior eye segment imaging module will be influenced, because the fixation point cannot move together with the four total-reflection mirrors in the optical path adjustment unit. Thus, the fixation optical path is definitely placed before the four total-reflection mirrors in the optical path adjustment unit. In one embodiment of the invention, the refraction adjustment unit 305 in the posterior eye segment imaging module and the refraction compensating lens 604 in the fixation optical module are concurrently moved by control of a computer to realize a co-moving mechanism between the refraction adjustment unit 305 and the refraction compensating lens 604. By moving concurrently the refraction adjustment unit 305 in the posterior eye segment imaging module and the refraction compensating lens 604 in the fixation optical module by the control of the computer, the fixation of human eye can be realized while the OCT optical path of the posterior eye segment imaging module would not be influenced.

It should be made clear that the fixation light output by the fixation device 601 in the fixation optical module can be visible light with a wavelength of 780 nm.

It should be made clear that the fixation device 601 in the fixation optical module comprises LCD or OLCD.

Figure 6:
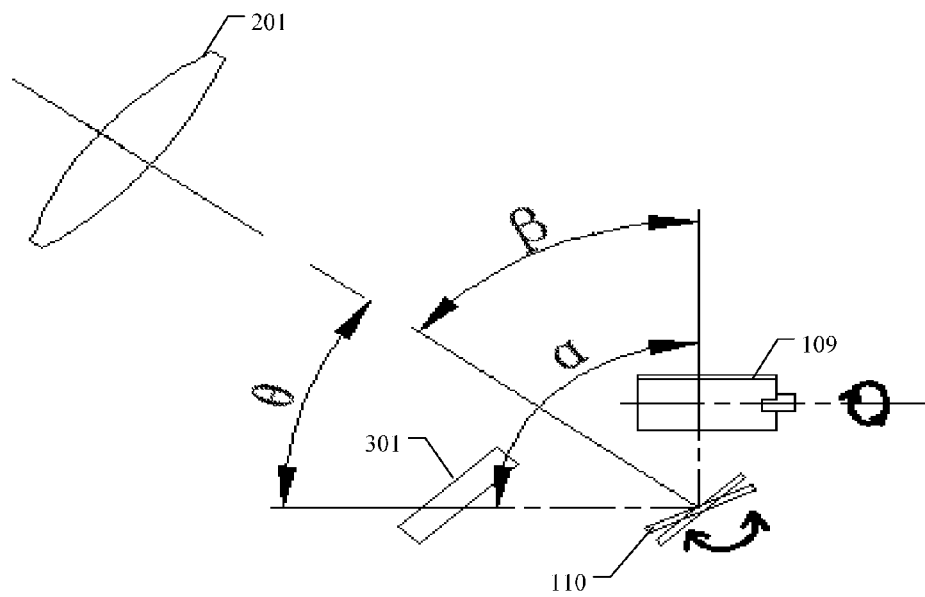
FIG. 6 is a schematic diagram of a method for quick switching to realize anterior and posterior eye segments imaging according to an embodiment of the invention.

FIG. 6 is a schematic diagram of a method of quick switching for realizing anterior and posterior eye segments imaging according to an embodiment of the invention. As shown in FIG. 6, the method comprises the following steps.

S101, when the Y-direction scanning unit is rotated at the first rotation angle, the Y-direction scanning unit reflects light transmitted from the X-direction scanning unit to the total-reflection mirror, which then reflects the light to the rotatable-adjustable total-reflection mirror. The rotatable-adjustable total-reflection mirror is rotatably adjusted according to the rotation of the Y-direction scanning unit and cooperates with the X-direction scanning unit to reflect the light transmitted on the rotatable-adjustable total-reflection mirror to the dichroic mirror. The light is then reflected to the fundus lens by the dichroic mirror and routed into the human eye E to be examined via the fundus lens.

Specifically, in one embodiment of the invention, the rotatable-adjustable total-reflection mirror 401 and the Y-direction scanning unit 110 are concurrently controlled by a computer. The Y-direction scanning unit is controlled by the computer to rotate at the first rotation angle. Here, the orientation of the Y-direction scanning unit is able to exactly make the angle between an incident light and a reflected light to be β. Concurrently, the computer controls the rotatable-adjustable total-reflection mirror 401 to rotate correspondingly to the first rotation angle of the Y-direction scanning unit 110 and to cooperate with the Y-direction scanning unit to realize anterior eye segment imaging. By rotating the Y-direction scanning unit 110, the light is transmitted to the total-reflection mirror 202 via the first relay lens 201 after it is routed through the Y-direction scanning unit. Then, the light is reflected by the total-reflection mirror 202, transmitted through the second relay lens 203, and transmitted to the rotatable-adjustable total-reflection mirror 401. The light is then reflected to the fundus lens 403 by the dichroic mirror 402. In the end, the light is routed through the human eye E and is focalized at the fundus.

S102, when the Y-direction scanning unit is rotated at the second angle, it reflects the light transmitted from the X-direction scanning unit into the optical path adjustment unit. The optical path adjustment unit reflects the light to the rotatable-adjustable total-reflection mirror via the refraction adjustment unit. The rotatable-adjustable total-reflection mirror is rotatably adjusted correspondingly to the rotation of the Y-direction scanning unit and cooperates with the Y-direction scanning unit to reflect the light transmitted on the rotatable-adjustable total-reflection mirror to the dichroic mirror. The light is then reflected to the fundus lens by the dichroic mirror and routed into the human eye E to be examined via the fundus lens.

Specifically, in one embodiment of the invention, the rotatable-adjustable total-reflection mirror 401 and the Y-direction scanning unit 110 are concurrently controlled by a computer. The Y-direction scanning unit is controlled by the computer to rotate at the second rotation angle. Here, the orientation of the Y-direction scanning unit is able to exactly make the angle between an incident light and a reflected light to be α. In the posterior eye segment imaging, it is required that the OCT light beam is focalized at the fundus when the scanning galvanometer is resting. Light transmitted from the X-direction scanning unit 109 is reflected to the optical path adjustment unit by the Y-direction scanning unit 110. Then, the light is reflected to the rotatable-adjustable total-reflection mirror 401 via the refraction adjustment unit 305 by the f optical path adjustment unit. The rotatable-adjustable total-reflection mirror 401 is rotated correspondingly to the second angle at which the Y-direction scanning unit 110 is rotated and cooperates with the Y-direction scanning unit 110 to implement the posterior eye segment imaging, reflecting the light transmitted on the rotatable-adjustable total-reflection mirror 401 to the dichroic mirror 402. The light is then reflected to the fundus lens by the dichroic mirror 402, routed through the human eye E, and focalized at the pupil of the human eye.

In one embodiment of the invention, the switch between the anterior and posterior eye segment optical paths is realized by mutual cooperation of the Y-direction scanning unit and the rotatable-adjustable total-reflection mirror.

Figure 8:
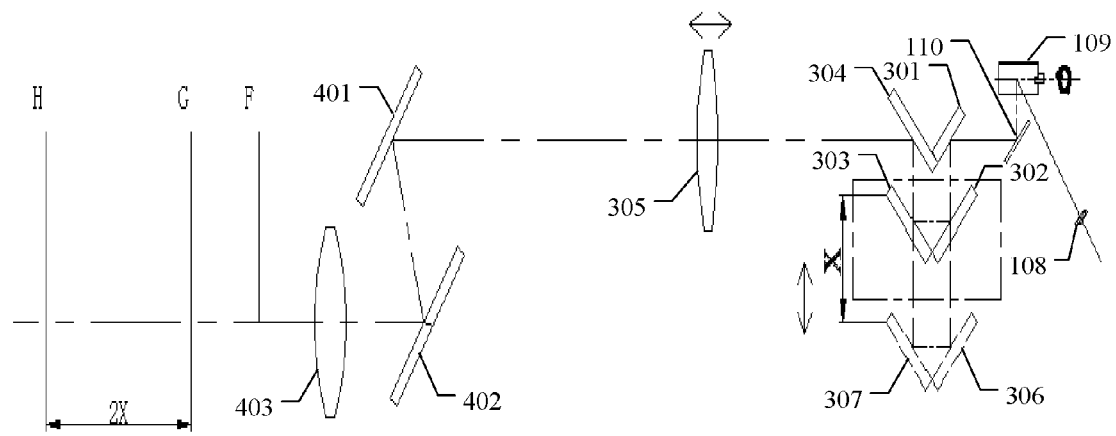
FIG. 8 is a schematic diagram of a method for eye axial length measurement based on quick switching between anterior and posterior eye segments imaging according to an embodiment of the invention.

FIG. 8 is a schematic diagram of eye axial length measurement based on quick switching between anterior and posterior eye segments imaging according to an embodiment of the invention. The method for measuring the eye axial length comprising the following steps.

S201, when the system is performing anterior eye segment imaging, an optical path length that light travels after leaving the fiber and before reaching a cornea of the human eye to be examined in the anterior eye segment imaging is obtained, the optical path length being a fixed length of anterior eye segment optical path plus a distance A between a peak of the cornea and a peak of image in an OCT image of anterior eye segment, wherein the fixed length of anterior eye segment optical path is an intrinsic parameter of the system, and the distance A between the peak of the cornea and the peak of image in the OCT image of anterior eye segment is obtained by analyzing the OCT image.

Specifically, when anterior eye segment imaging is implemented in the system according to one embodiment of the invention, the rotatable-adjustable total-reflection mirror 401 is rotated correspondingly to the first angle at which the Y-direction scanning unit is rotated and cooperates with the Y-direction scanning unit to realize the anterior eye segment imaging. The light beam is routed through the Y-direction scanning unit, transmitted to the total-reflection mirror 202 via the first relay lens 201, reflected to the rotatable-adjustable total-reflection mirror 401 via the second relay lens 203 by the total-reflection mirror 202, reflected to the fundus lens 403 via the dichroic mirror 402, and transmitted into the human eye E in the end. The optical path length that light travels after leaving the fiber and before reaching a cornea of the human eye to be examined is a fixed length of anterior eye segment optical path plus a distance A between a peak of the cornea and a peak of image in an OCT image of anterior eye segment, wherein the fixed length of anterior eye segment optical path is an intrinsic parameter of the system, and the distance A between the peak of the cornea and the peak of image in the OCT image of anterior eye segment is obtained by analyzing the OCT image. When anterior eye segment imaging is implemented in the system according to one embodiment of the invention, the aplanatic plane of the anterior eye segment imaging optical path locates at F in FIG. 8.

S202, when the system is performing posterior eye segment imaging, an optical path length that light travels after leaving the fiber and before reaching a retina of the human eye to be examined in the posterior eye segment imaging is obtained, the optical path length being a fixed length of posterior eye segment optical path plus an optical path adjustment amount plus a distance B between a peak of image and a macula fovea in an OCT image of posterior eye segment, wherein the fixed length of posterior eye segment optical path is an intrinsic parameter of the system, and the distance B between the peak of image and the macula fovea in the OCT image of posterior eye segment is obtained by analyzing the OCT image.

Specifically, when anterior eye segment imaging is implemented in the system according to one embodiment of the invention, the Y-direction scanning unit reflects the light transmitted from the X-direction scanning unit to the optical path adjustment unit. The light is then reflected to the rotatable-adjustable total-reflection mirror 401 via the refraction adjustment unit 305 by the optical path adjustment unit, reflected to the fundus 403 via the dichroic mirror 402, transmitted into the human eye E, and focalized at the pupil of the human eye E. The optical path length that light travels after leaving the fiber and before reaching a retina of the human eye to be examined in the posterior eye segment imaging is a fixed length of posterior eye segment optical path plus an optical path adjustment amount plus a distance B between a peak of image and a macula fovea in an OCT image of posterior eye segment, wherein the fixed length of posterior eye segment optical path is an intrinsic parameter of the system, and the distance B between the peak of image and the macula fovea in the OCT image of posterior eye segment is obtained by analyzing the OCT image. The aplanatic plane of the posterior eye segment imaging optical path locates at G in FIG. 8, and the aplanatic plane of the fundus optical path locates at H in FIG. 8.

S203, a difference between the optical path length obtained in anterior eye segment imaging and the optical path length obtained in posterior eye segment imaging is calculated, and an optical length of examined eye axis is obtained, wherein the optical length of eye axis is: (the fixed length of posterior eye segment optical path plus an optical path adjustment amount plus the distance B between the peak of image and the macula fovea in the OCT image of posterior eye segment) minus (the fixed length of anterior eye segment optical path plus the distance A between the peak of the cornea and the peak of image in the OCT image of anterior eye segment). Based on the optical length of eye axis, the length of the eye axis may be obtained, namely, the length of the eye axis is equal to the optical length of eye axis divided by the refractive index of the eye.

Specifically, in one embodiment of the invention, when the removable total-reflection mirrors 302 and 303 are at original positions, the optical path difference between the aplanatic plane (at location G in FIG. 8) of the fundus optical path and the aplanatic plane (at location F in FIG. 8) of the anterior eye segment imaging optical path is C0, which can be measured by calibrations. Axis lengths of different human beings are different. When implementing OCT imaging of the fundus, the aplanatic plane of fundus imaging optical path locates at position G in FIG. 8. Fundus imaging for different human eyes are realized by moving the removable total-reflection mirrors 302 and 303 up-and-down. Hence, when the total-reflection mirrors 302 and 303 are concurrently down moved for a distance X, the position of the aplanatic plane of fundus imaging optical path is changed from 306 to 307, varying for a distance 2x.

Figure 7:
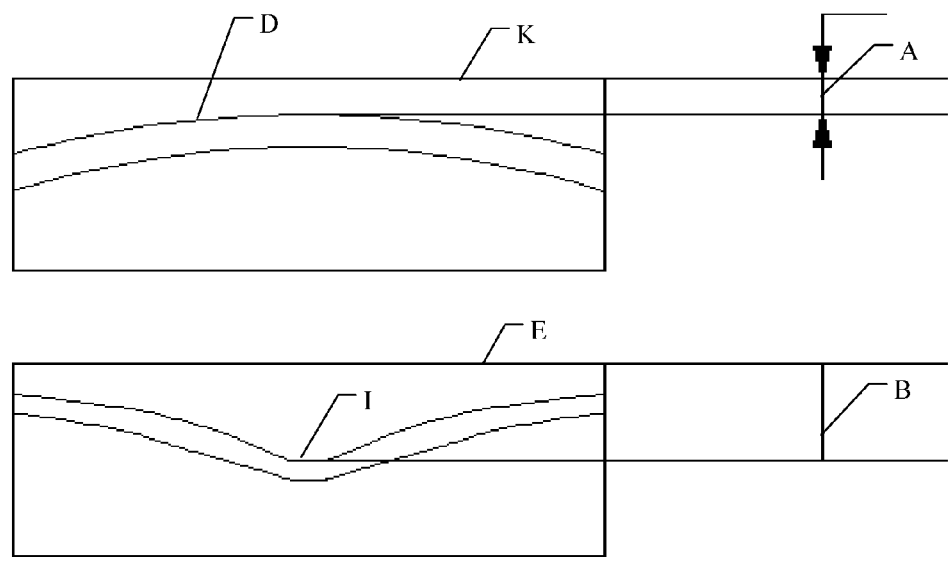
FIG. 7 is a schematic diagram of a structure for eye axial length measurement based on quick switching between anterior and posterior eye segments imaging according to an embodiment of the invention.

In one embodiment of the invention, measurement of axis length is realized based on anterior and posterior eye segments imaging. Steps of the measurement of axis length are illustrated in FIGS. 7 and 8. FIG. 7 comprises the following: the peak K of the cornea in the anterior eye segment OCT image, the peak D of image in the anterior eye segment OCT image, the distance A between the peak of the cornea and the peak of image in the anterior eye segment OCT image, the peak E of image in the posterior eye segment OCT image, the macula fovea I in the posterior eye segment OCT image, and the distance B between the peak of image and the macula fovea in the posterior eye segment OCT image. The specific operation steps are as below: firstly, the removable total-reflection mirrors 302 and 303 are reset. Here, the fixed difference between optical paths for anterior and posterior eye segments is C0, which is obtained by calibrations. That is, by resetting the removable total-reflection mirrors 302 and 303 to quick switch between anterior and posterior eye segments optical paths and to move the examined object back-and-forth, the OCT signals of the object is located at the same position in the anterior and posterior eye segment OCT images, namely, distances of the interference planes from the peaks of images are the same. By measuring the back-and-forth movement amount of the object, calibrations can be determined to obtain the value of the fixed difference C0 between optical paths for anterior and posterior eye segments. Then, the cornea is placed at the location F shown in FIG. 8, and at the same time, the removable total-reflection mirrors 302 and 303 are quickly moved to obtain an OCT image of the human eye retina. OCT images of the anterior and posterior eye segments are obtained after quick imaging of the anterior and posterior eye segments, wherein the movement amount of the removable total-reflection mirrors 302 and 303 is X. They are respectively used to measure distance A between the peak of cornea and the peak of image in the OCT image of the anterior eye segment, and distance B between the peak of image and the macula fovea in the OCT image of the posterior eye segment. Thus, length difference between optical paths for the anterior and posterior eye segments are C=C0±2x, wherein "±" is determined by moving the removable total-reflection mirrors 302 and 303 up or down, and C0 is a fixed length difference between optical paths for the anterior and posterior eye segments. In the end, the optical length of human eye axis is L=B+C−A. That is, the optical length of eye axis is equal to distance B between the peak of image and the macula fovea in the OCT image of the posterior eye segment plus length difference between optical paths for the anterior and posterior eye segments minus distance A between the peak of cornea and the peak of image in the OCT image of the anterior eye segment.

It should be made clear that an ophthalmic optical coherence tomography system provided in an embodiment of the invention can further be used to measure the depth of anterior chamber. The method for measuring the depth of anterior chamber has the same principle of the measurement of eye axial length. When the system is performing anterior eye segment imaging, an anterior surface of corneal in a cornea image in the anterior eye segment imaging optical path is collected, and the length of posterior eye segment imaging optical path is changed by adjusting a removable total-reflection mirror, i.e. the second total-reflection mirror 302 and the third total-reflection mirror 303, or a removable retroreflector in the optical path adjustment unit, so that a surface of crystalline lens is measured to obtain an optical depth of anterior chamber, the optical depth of anterior chamber being a distance between the cornea and an anterior surface of crystalline lens, wherein the anterior surface of corneal is obtained with a anterior eye segment imaging system and the anterior surface of crystalline lens is obtained with a posterior eye segment imaging system.

Based on the obtained optical depth of anterior chamber, the depth of anterior chamber can be obtained, wherein the depth of anterior chamber is dividing the optical depth of anterior chamber by the refractive index of the anterior chamber.

It should be made clear that an ophthalmic optical coherence tomography system provided in an embodiment of the invention can further be used to measure the thickness of crystalline lens. When the system is performing anterior eye segment imaging, a cornea image in the anterior eye segment imaging optical path is collected, and the length of posterior eye segment imaging optical path is changed by adjusting a removable total-reflection mirror or a removable retroreflector in the optical path adjustment unit, so that a posterior surface of crystalline lens is measured with the posterior eye segment imaging optical path. Then, a distance between the cornea and the posterior surface of crystalline lens is obtained. An optical thickness of the crystalline lens is obtained by subtracting the distance by the optical depth of anterior chamber.

Optionally, the anterior surface of crystalline lens is scanned with the anterior eye segment imaging optical path and concurrently, the posterior surface of crystalline lens is collected with the posterior eye segment imaging optical path, to obtain the optical thickness of the crystalline lens. The optical thickness of the crystalline lens is equal to subtracting the posterior surface of crystalline lens collected with the posterior eye segment imaging optical path by the anterior surface of crystalline lens scanned with the anterior eye segment imaging optical path.

Based on the optical thickness of crystalline lens, the thickness of crystalline lens can be obtained, wherein the thickness of crystalline lens is dividing the optical thickness of crystalline lens by the refractive index of the crystalline lens.

It should be made clear that in the optical paths for anterior and posterior eye segments, in order to measure the anterior and posterior surfaces of the crystalline lens, lens may be inserted in any one or both of the optical paths for anterior and posterior eye segments to change the positions of the optical path focal points, so as to make the focal points of the optical paths are just located on the anterior and posterior surfaces of the crystalline lens.

A person having ordinary skills in the art can realize that part or whole of the processes in the methods according to the above embodiments may be implemented by a computer program giving instructions to relevant hardwares. The program may be stored in a computer readable storage medium. When executed, the program may comprise processes in the above-mentioned embodiments of methods. The storage medium may be a magnetic disk, an optical disk, a Read-Only Memory (ROM), a Random Access Memory (RAM), et al.

The above descriptions are preferred embodiments of the invention. It should be pointed out that a person having ordinary skills in the present technical field will be able to make improvements and modifications within the spirit of the principle of the invention. The improvements and modifications should also be incorporated in the protection scope of the invention.

What is claimed is:

1. A method for switching to realize anterior and posterior eye segments imaging, comprising:
    reflecting light transmitted from a X-direction scanning unit to a total-reflection mirror with a Y-direction scanning unit when the Y-direction scanning unit is rotated at the first rotation angle; reflecting the light to a rotatable-adjustable total-reflection mirror with the total-reflection mirror, the rotatable-adjustable total-reflection mirror being rotatably adjusted correspondingly to a rotation of the Y-direction scanning unit and cooperating with the Y-direction scanning unit to reflect the light transmitted on the rotatable-adjustable total-reflection mirror to a dichroic mirror; reflecting the light to the fundus lens with the dichroic mirror; transmitting the light through the fundus lens into a human eye to be examined;
    reflecting the light transmitted from the X-direction scanning unit to an optical path adjustment unit with the Y-direction scanning unit when the Y-direction scanning unit is rotated at a second rotation angle; reflecting the light to the rotatable-adjustable total-reflection mirror via a refraction adjustment unit with the optical path adjustment unit, the rotatable-adjustable total-reflection mirror being rotatably adjusted correspondingly to the rotation of the Y-direction scanning unit and cooperating with the Y-direction scanning unit to reflect the light transmitted on the rotatable-adjustable total-reflection mirror to the dichroic mirror; reflecting the light to the fundus lens with the dichroic mirror; and transmitting the light through the fundus lens into the human eye to be examined.

2. The method as claimed in claim 1, comprising:
    when the system is performing anterior eye segment imaging, obtaining an optical path length that the light travels after leaving the fiber and before reaching a cornea of the human eye to be examined in the anterior eye segment imaging, the optical path length being a fixed length of anterior eye segment optical path plus a distance A between a peak of the cornea and a peak of image in an OCT image of anterior eye segment, wherein the fixed length of anterior eye segment optical path is an intrinsic parameter of the system, and the distance A between the peak of the cornea and the peak of image in the OCT image of anterior eye segment is obtained by analyzing the OCT image;
    when the system is performing posterior eye segment imaging, obtaining an optical path length that the light travels after leaving the fiber and before reaching a retina of the human eye to be examined in the posterior eye segment imaging, the optical path length being a fixed length of posterior eye segment optical path plus an optical path adjustment amount plus a distance B between a peak of image and a macula fovea in an OCT image of posterior eye segment, wherein the fixed length of posterior eye segment optical path is an intrinsic parameter of the system, and the distance B between the peak of image and the macula fovea in the OCT image of posterior eye segment is obtained by analyzing the OCT image;
    calculating a difference between the optical path length obtained in the anterior eye segment imaging and the optical path length obtained in the posterior eye segment imaging, and obtaining an optical length of examined eye axis, wherein the optical length of eye axis is: the sum of the fixed length of posterior eye segment optical path plus the optical path adjustment amount plus the distance B between the peak of image and the macula fovea in the OCT image of posterior eye segment minus the sum of the fixed length of anterior eye segment optical path plus the distance A between the peak of the cornea and the peak of image in the OCT image of anterior eye segment.

3. The method as claimed in claim 1, comprising:
    when the system is performing anterior eye segment imaging, collecting an anterior surface of corneal in a cornea image in the anterior eye segment imaging optical path, and changing the length of posterior eye segment imaging optical path by adjusting a removable total-reflection mirror or a removable retroreflector in the optical path adjustment unit, so that a surface of crystalline lens is measured to obtain an optical depth of anterior chamber, the optical depth of anterior chamber being a distance between the cornea and an anterior surface of crystalline lens, wherein the anterior surface of corneal is obtained with a anterior eye segment imaging system and the anterior surface of crystalline lens is obtained with a posterior eye segment imaging system.

4. The method as claimed in claim 1, comprising:
    when the system is performing anterior eye segment imaging, collecting a cornea image in the anterior eye segment imaging optical path; changing a length of posterior eye segment imaging optical path by adjusting a removable total-reflection mirror or a removable retroreflector in the optical path adjustment unit, so that a posterior surface of crystalline lens is measured with the posterior eye segment imaging optical path; obtaining a distance between the cornea and the posterior surface of crystalline lens; and obtaining an optical thickness of the crystalline lens by subtracting the distance by the optical depth of anterior chamber; or scanning an anterior surface of crystalline lens with the anterior eye segment imaging optical path and concurrently collecting the posterior surface of crystalline lens with the posterior eye segment imaging optical path, to obtain the optical thickness of the crystalline lens, the optical thickness of the crystalline lens being equal to subtracting the posterior surface of crystalline lens collected with the posterior eye segment imaging optical path by the anterior surface of crystalline lens scanned with the anterior eye segment imaging optical path.

* * * * *